(12) United States Patent
Tanida et al.

(10) Patent No.: US 11,703,434 B2
(45) Date of Patent: Jul. 18, 2023

(54) CONCENTRATION MEASURING DEVICE (71) Applicant: AISAN KOGYO KABUSHIKI KAISHA, Obu (JP)

(72) Inventors: Yuya Tanida, Obu (JP); Mariko Kawase, Funabashi (JP)

(73) Assignee: AISAN KOGYO KABUSHIKI KAISHA, Obu (JP)

( * ) Notice: Subject to any disclaimer, the term of this patent is extended or adjusted under 35 U.S.C. 154(b) by 0 days.

(21) Appl. No.: 17/729,164

(22) Filed: Apr. 26, 2022

(65) Prior Publication Data
US 2022/0349795 A1    Nov. 3, 2022

(30) Foreign Application Priority Data

Apr. 30, 2021   (JP) ................. 2021-077345

(51) Int. Cl.
*F02D 41/00*    (2006.01)
*G01N 7/14*    (2006.01)
*G01N 7/04*    (2006.01)
*G01N 33/22*    (2006.01)

(52) U.S. Cl.
CPC ........... *G01N 7/14* (2013.01); *F02D 41/0045* (2013.01); *G01N 7/04* (2013.01); *F02D 2200/0602* (2013.01); *G01N 33/225* (2013.01)

(58) Field of Classification Search
CPC ........ F02D 41/0045; F02D 2200/0602; G01N 7/14; G01N 7/04; G01N 33/225; G01N 15/06; G01N 2015/0026

USPC ................. 123/518–520, 522, 523; 701/107; 73/114.39

See application file for complete search history.

(56) References Cited

U.S. PATENT DOCUMENTS

| | | |
|---|---|---|
| 7,272,485 B2 | 9/2007 | Amano et al. |
| 7,373,929 B2 | 5/2008 | Amano et al. |
| 7,389,769 B2 | 6/2008 | Amano et al. |
| 9,689,341 B2 * | 6/2017 | Pursifull ............. F02D 41/3854 |

FOREIGN PATENT DOCUMENTS

| | | |
|---|---|---|
| JP | 2006046261 A | 2/2006 |
| JP | 2017180321 A | 10/2017 |

* cited by examiner

*Primary Examiner* — Hai H Huynh
(74) *Attorney, Agent, or Firm* — Conley Rose, P.C.

(57) ABSTRACT

A concentration measuring device includes a circulation passage, an aspirator, a differential pressure sensor, and a control unit. The aspirator is disposed in a fuel tank and is connected to the circulation passage. While a gas flows from a gaseous layer within a fuel tank through the circulation passage due to a negative pressure generated in the aspirator, the differential pressure sensor measures a pressure difference of the gas within the circulation passage between an upstream side of a narrowed part, having a narrower passage area than an adjacent portion of the circulation passage, and a downstream side of the narrowed part. The control unit is configured to calculate a density of the fuel vapor from the pressure difference of the gas and to calculate a concentration of the fuel vapor from the density of the fuel vapor.

3 Claims, 7 Drawing Sheets

CONCENTRATION MEASURING DEVICE

CROSS-REFERENCE TO RELATED APPLICATIONS

This application claims priority to Japanese patent application serial number 2021-077345, filed Apr. 30, 2021, which is hereby incorporated herein by reference in its entirety for all purposes.

STATEMENT REGARDING FEDERALLY SPONSORED RESEARCH OR DEVELOPMENT

Not applicable.

BACKGROUND

This disclosure relates generally to concentration measuring devices.

One type of concentration measuring device is provided for a vehicle having an engine for measuring a fuel vapor concentration in a fuel tank of the vehicle. The concentration measuring device includes a measuring passage, a switching valve capable of connecting the measuring passage to either a gaseous layer in the fuel tank or the atmosphere in a fluid communication state, and a pump configured to generate a flow of a gas, such as fuel vapor or air, in the measuring passage. A constriction part is formed at the middle of the measuring passage. The concentration measuring device is configured to measure the fuel vapor concentration from a pressure difference of the fuel vapor and/or the air, which is flowed by the pump, between before and after having passed through the constriction part.

SUMMARY

In one aspect of this disclosure, a concentration measuring device includes an aspirator, a circulation passage, a fuel pump, a differential pressure sensor, and a control unit. The aspirator is disposed in a fuel tank and includes a decompression chamber. The circulation passage connects a gaseous layer in the fuel tank to the decompression chamber of the aspirator. The circulation passage includes a narrowed part having a narrower passage area than an adjacent portion of the circulation passage. The fuel pump is configured to pump a liquid fuel stored in the fuel tank to the aspirator. While the liquid fuel pumped by the fuel pump flows through an internal space of the aspirator, the aspirator generates a negative pressure in the decompression chamber so as to flow a gas containing a fuel vapor from the gaseous layer of the fuel tank through the circulation passage. The differential pressure sensor is configured to measure a pressure difference of the gas within the circulation passage between an upstream portion of the circulation passage in which the gas flows before passing through the narrowed part and a downstream portion of the circulation passage in which the gas flows after passing through the narrowed part. The control unit implemented by at least one programmed processor and is configured to calculate a density of the gas from the pressure difference of the gas, to calculate a density of the fuel vapor from the density of the gas, and to calculate a concentration of the fuel vapor from the density of the fuel vapor.

DETAILED DESCRIPTION

Japanese Laid-Open Patent Publication No. 2006-46261 discloses a concentration measuring device to measure a fuel vapor concentration from a pressure difference of a fuel vapor and/or an air, which is flowed by a pump, upstream and downstream of a constriction part along a measuring passage. The pump of the concentration measuring device is provided on the measuring passage. Thus, heat generated by the pump can affect the fuel vapor and/or the air flowing through the measuring passage. Therefore, there has been a need for improved concentration measuring devices.

An embodiment of this disclosure will now be described based on FIGS. 1-13. In the following descriptions, orientations, such as upper, lower, right, and left, correspond to directions illustrated in each drawing.

Figure 1:
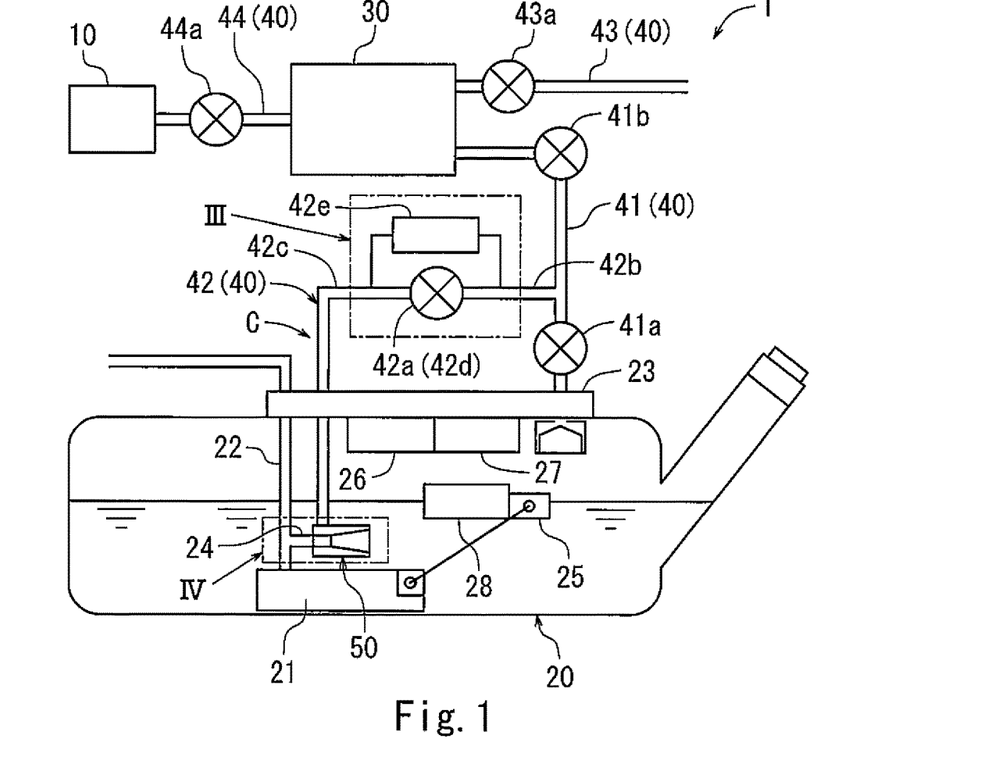
FIG. 1 is a schematic view of an embodiment of a fuel vapor processing system, which includes a leakage detector in accordance with the principles described herein.

Referring now to FIG. 1, a fuel vapor processing system 1 according to a first embodiment is configured such that fuel vapor evaporated in a fuel tank 20 of a vehicle is introduced into an engine 10, so as to prevent the fuel vapor from flowing to the surrounding outside environment. As will be described in more detail below, the fuel vapor processing system 1 is equipped with a leakage detector, a concentration measuring device, and a convective velocity measuring device.

Figure 2:
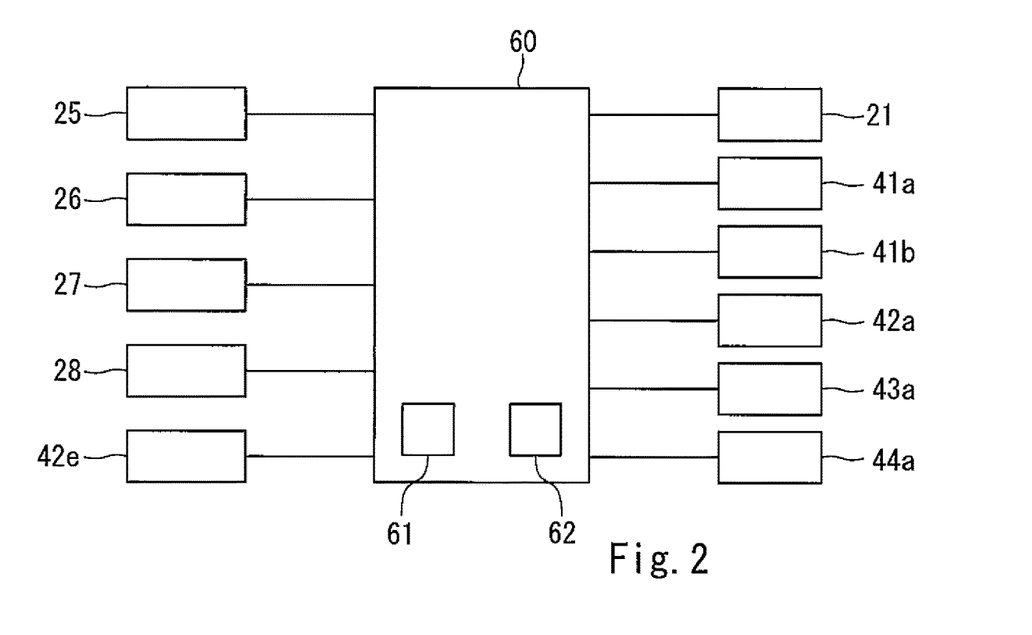
FIG. 2 is a schematic view of an embodiment of an electronic control unit incorporated in the fuel vapor processing system of FIG. 1.

As shown in FIG. 1, the fuel vapor processing system 1 includes the engine 10, the fuel tank 20, a canister 30, and vapor piping 40. The engine 10 runs on liquid fuel, such as gasoline. The fuel tank 20 stores the liquid fuel that is supplied to the engine 10. The canister 30 is in fluid communication with the fuel tank 20 and is configured to adsorb and desorb fuel vapor evaporated in the fuel tank 20. The vapor piping 40 connects the engine 10, the fuel tank 20, and the canister 30 to each other and is configured to flow the fuel vapor therethrough. As shown in FIG. 2, the fuel vapor processing system 1 includes an electronic control unit (ECU) 60 configured to control the engine 10, among other components. The ECU 60 may be implemented by at least one programmed processor whose operation is determined by a predetermined program, gate arrays, and/or the like. As shown in FIG. 1, an interior space of the fuel tank 20 is divided into a liquid layer composed of the liquid fuel and a gaseous layer composed of the fuel vapor and air.

The canister 30 houses an adsorbent, such as activated carbon, therein. The adsorbent is configured to trap and adsorb the fuel vapor and not to adsorb air. That is, air can freely pass through the canister 30 filled with the adsorbent. As shown in FIG. 1, the canister 30 is in fluid communication with each of the fuel tank 20, the engine 10, and the atmosphere. More specifically, the canister 30 is in fluid communication with the gaseous layer of the fuel tank 20 via a vapor passage 41, a shut-off valve 41a, and a closing valve 41b. The canister 30 is in fluid communication with the engine 10 via a purge passage 44 and a purge valve 44a. The canister 30 is in fluid communication with the atmosphere via an atmospheric passage 43 and an atmospheric valve 43a.

In accordance with the above-described configuration, when the internal pressure of the fuel tank 20 becomes higher than atmospheric pressure in a state where the shut-off valve 41a, the closing valve 41b, and the atmospheric valve 43 are open, a gaseous mixture which includes air and fuel vapor flows from the gaseous layer of the fuel tank 20 into the canister 30 via the vapor passage 41. When the gaseous mixture flows into the canister 30, the fuel vapor contained in the gaseous mixture is trapped and adsorbed on the adsorbent. On the other hand, the air contained in the gaseous mixture flows through the canister 30 and is released into the atmosphere via the atmospheric passage 43. In this way, the canister 30 is configured to prevent the fuel vapor from flowing to the outside while also depressurizing the fuel tank 20. When the engine 10 is running and the purge valve 44a is open, the intake negative pressure generated by the engine 10 is applied to the canister 30. In such condition, the fuel vapor trapped and adsorbed in the canister 30 is desorbed from the adsorbent and is introduced into the engine 10 via the purge passage 44.

The fuel tank 20 includes a set plate 23 that is removably attached to an upper surface of the fuel tank 20.

As shown in FIG. 1, the fuel tank 20 includes a fuel pump 21 and a supply pipe 22. The fuel pump 21 is located in the fuel tank 20 and is positioned on a bottom of the fuel tank 20. The supply pipe 22 extends from the fuel pump 21 through the set plate 23 to the engine 10. The fuel pump 21 is configured to pump the liquid fuel from the fuel tank 20 to the engine 10 via the supply pipe 22. The fuel tank 20 includes a branch passage 24 and an aspirator 50. The branch passage 24 branches from the supply pipe 22 in the liquid layer. The aspirator 50 is attached to a free end of the branch passage 24. Thus, when the fuel pump 21 pumps the liquid fuel toward the engine 10, a part of the liquid fuel flows through the branch passage 24 and then is jetted from the aspirator 50 toward the liquid layer. Due to this jet, the aspirator 50 generates negative pressure therein by the Venturi effect.

The fuel tank 20 includes a level sensor for detecting a remaining amount of the liquid fuel in the fuel tank 20. The level sensor includes a rotatable arm, and a float 25 that is attached to a free end of the arm and is configured to float on the surface of the liquid fuel. The level sensor is configured to measure the remaining amount of the liquid fuel based on an angle of the arm. The fuel tank 20 includes a pressure sensor 26 disposed in the gaseous layer. The pressure sensor 26 is configured to measure the pressure of the gaseous layer within the fuel tank 20. The fuel tank 20 includes a first temperature sensor 27 and a second temperature sensor 28. The first temperature sensor 27 is disposed on a lower surface of the set plate 23. The second temperature sensor 28 is attached to the float 25. The first temperature sensor 27 is configured to measure temperature at an upper region of the gaseous layer of the fuel tank 20. The second temperature sensor 28 is configured to measure temperature at a lower region of the gaseous layer of the fuel tank 20.

As shown in FIG. 1, the vapor piping 40 includes a suction passage 42 branching from the vapor passage 41, in addition to the vapor passage 41, the atmospheric passage 43, and the purge passage 44. The suction passage 42 branches from a portion of the vapor passage 41 on the fuel tank 20 side of the closing valve 41b. In other words, the suction passage 42 branches from a portion of the vapor passage 41 between the shut-off valve 41a and the closing valve 41b. The suction passage 42 extends into the fuel tank 20 and is connected to the aspirator 50. Due to this configuration, the vapor passage 41 and the suction passage 42 form a circulation passage C that is configured to circulate the gaseous mixture of the gaseous layer of the fuel tank 20 between the inside and the outside of the fuel tank 20.

Figure 3:
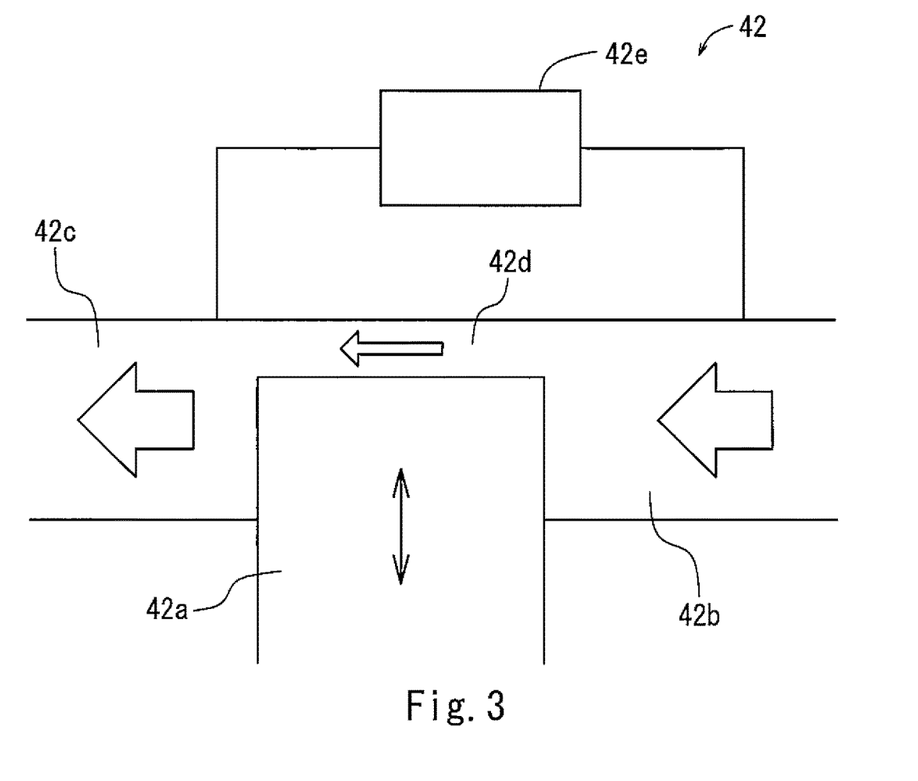
FIG. 3 is an enlarged schematic view of a section III of FIG. 1.

A multistage shut-off valve 42a is provided in a middle portion of the suction passage 42 to form a narrowed part 42d. The narrowed part 42d of the suction passage 42 has a narrowed passage width, which may be narrower than the passage width of the suction passage 42. The multistage shut-off valve 42a is connected to a stepping motor or the like, and is configured to change an opening amount of the multistage shut-off valve 42a. As shown in FIG. 3, the passage width of the suction passage 42 is varied depending on the opening amount of the multistage shut-off valve 42a. The suction passage 42 includes an upstream suction passage 42b and a downstream suction passage 42c, such that the upstream suction passage 42b is connected to the downstream suction passage 42c via the narrowed part 42d. The suction passage 42 is provided with a differential pressure sensor 42e configured to measure a pressure difference of the gaseous mixture before and after having passed through the narrowed part 42d.

The suction passage 42 is in fluid communication with the aspirator 50, so that the negative pressure generated in the aspirator 50 is applied to the suction passage 42. Thus, when the negative pressure is applied under a state where the shut-off valve 41a and the multistage shut-off valve 42a are open and where the closing valve 41b is closed, the gaseous mixture flows from the gaseous layer of the fuel tank 20, through the vapor passage 41 and the suction passage 42, and then returns to the gaseous layer. Further, the internal pressure of the downstream suction passage 42c can be decreased to be made negative when the aspirator 50 generates the negative pressure under a state where the multistage shut-off valve 42a is closed.

Figure 4:
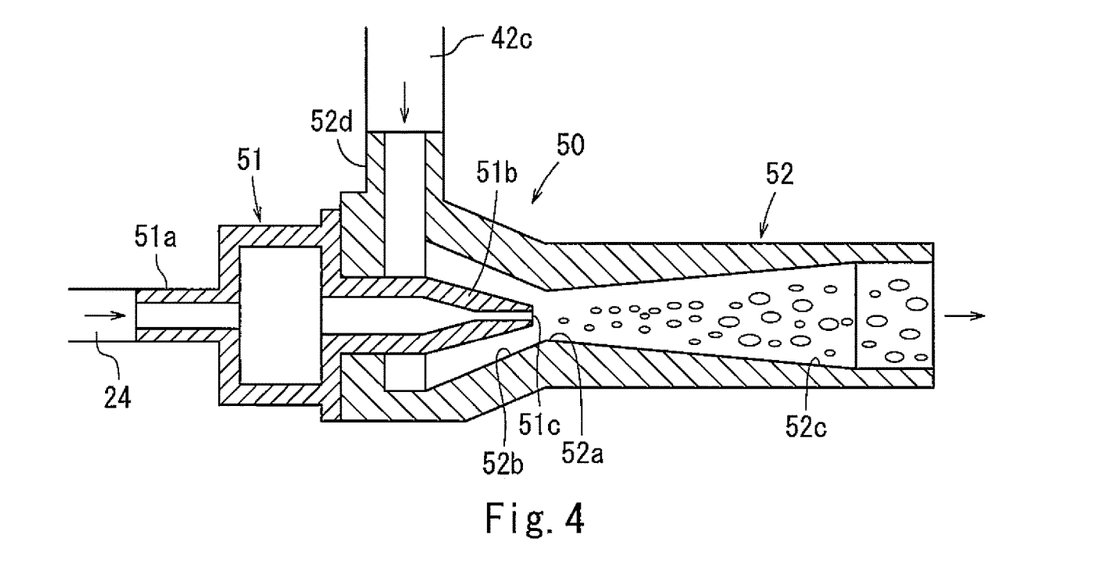
FIG. 4 is an enlarged schematic view of a section IV of FIG. 1.

As shown in FIG. 4, the aspirator 50 includes a nozzle part 51 configured to jet the liquid fuel. The aspirator 50 also includes a venturi part 52 configured to generate a negative pressure due to the liquid fuel jet from the nozzle part 51. The nozzle part 51 includes an inflow port 51a and a nozzle body 51b. The inflow port 51a is connected to the branch passage 24, such that the liquid fuel flows from the branch passage 24 and into the nozzle part 51 via the inflow port 51a. The nozzle body 51b has a jet port 51c at one end thereof and is configured to jet the fuel from the jet port 51c toward the venturi part 52. The venturi part 52 substantially has a cylindrical shape and includes a constricted section 52a, a decompression chamber 52b, and a diffuser 52c therein, all of which are coaxially aligned. The inner diameter of the decompression chamber 52b gradually decreases in a discharge direction of the liquid fuel from the nozzle body 51b. The inner diameter of the diffuser 52c gradually increases in the discharge direction of the liquid fuel. The constricted section 52a is positioned between the decompression chamber 52b and the diffuser 52c, such that the inner diameter of the venturi part 52 is the smallest at the constricted section 52a. The venturi part 52 includes a suction port 52d, such that the decompression chamber 52b is in fluid communication with the downstream suction passage 42c via the suction port 52d.

As shown in FIG. 4, the nozzle part 51 is coaxially attached to the venturi part 52. Thus, the nozzle body 51b of the nozzle part 51 is inserted into the venturi part 52 from the decompression chamber 52b side of the venture part 52, such that the jet port 51c is positioned close to and in front (in the direction of fluid flow) of the constricted section 52a. Due to this configuration, the fuel discharged from the jet port 51c flows through the constricted section 52a and the diffuser 52c at high speed in an axial direction of these parts. As a result, a negative pressure is generated in the decompression chamber 52b by the Venturi effect.

As shown in FIG. 2, the ECU 60 includes a processor 61 and a memory unit 62. The memory unit 62 may be formed of any suitable component, including a read-only memory, a random-access memory, or the like. The ECU 60 is configured to perform the leakage diagnosis with the processor 61 by operating programs stored in the memory unit 62. The ECU 60 receives measurement signals from the float 25, the pressure sensor 26, the first temperature sensor 27, the second temperature sensor 28, and the differential pressure sensor 42e. Further, the ECU 60 transmits control signals to the fuel pump 21, the shut-off valve 41a, the closing valve 41b, the multistage shut-off valve 42a, the atmospheric valve 43a, and the purge valve 44a, so as to control them.

A method for detecting vapor leakage from the fuel tank 20 will be described based on the fuel vapor processing system 1. In brief, after closing the shut-off valve 41a, the closing valve 41b, and the multistage shut-off valve 42a in a state where the internal pressure of the fuel tank 20 is positive, temporal changes of the internal pressure of the fuel tank 20 are measured by the pressure sensor 26. When the internal pressure of the fuel tank 20 is less than a reference pressure after a predetermined period of time has elapsed from when the valves 41a, 41b, 42a were closed, it is determined that leakage from the fuel tank 20 occurs. The reference pressure corresponds to a diagnostic criteria previously calculated by or stored in the ECU 60.

Figure 5:
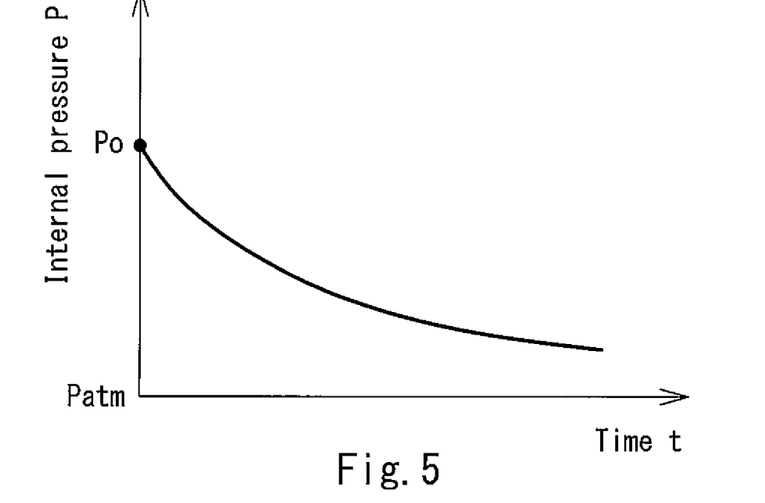
FIG. 5 is a graph showing temporal changes of a non-corrected reference pressure.

The detection method of the vapor leakage will be described in more detail. First, the ECU 60 calculates the reference pressure, which may correspond to a virtual temporal change of the internal pressure of the fuel tank 20. In this embodiment, the virtual temporal change is calculated based on Bernoulli's theorem, or the like, which may be further based on the assumption that an initial internal pressure P0 of the closed fuel tank 20 is higher than atmospheric pressure Patm, and that the fuel tank 20 has a circular opening, having an inner diameter of 0.5 mm, in fluid communication with the outside. An example of the calculated reference pressure is shown in FIG. 5. However, in some embodiments, the initial pressure P0 may be less than atmospheric pressure Patm. In such case, when the internal pressure of the fuel tank 20 is higher than the calculated reference pressure after a predetermined period of time has elapsed from when the valves 41a, 41b, 42a were closed, it is determined that leakage from the fuel tank 20 has occurred.

The internal pressure of the fuel tank 20 is influenced by changes in the fuel vapor pressure in the gaseous layer of the fuel tank 20. Thus, it has been discovered that it is beneficial to estimate the temporal change of the fuel vapor pressure and then to correct the reference pressure based on the estimated temporal change of the fuel vapor pressure. Specifically, the reference pressure is corrected such that as the vapor pressure becomes higher, the reference pressure becomes higher, and such that as the vapor pressure becomes lower, the reference pressure becomes lower. It was discovered that the temporal change of the vapor pressure can be estimated based on certain characteristics, such as the saturation vapor pressure, partial pressure (or concentration) of the fuel vapor in the gaseous mixture, and convective velocity of the gaseous mixture in the gaseous layer.

Figure 6:
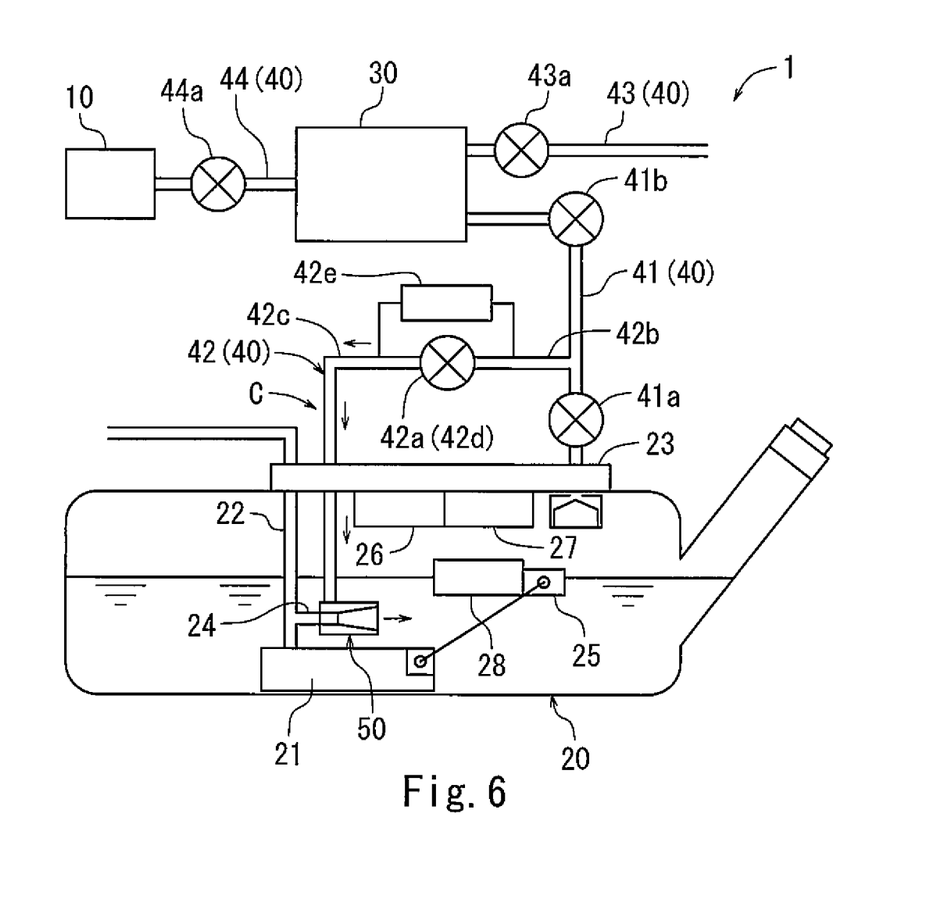
FIG. 6 is a schematic view of the fuel vapor processing system of FIG. 1 in a state where a saturation vapor pressure curve is estimated.

The characteristic of the saturation vapor pressure may be represented by a saturation vapor pressure curve. Thus, in order to estimate the temporal change, the ECU 60 is configured to specify the saturation vapor pressure curve showing a relationship between the temperature in the gaseous layer and the saturation vapor pressure of the fuel vapor. As shown in FIG. 6, the fuel pump 21 is driven to forcedly feed the liquid fuel under a state where the multistage shut-off valve 42a is closed. When the pumped liquid fuel flows through the aspirator 50, a negative pressure is generated in the decompression chamber 52b of the aspirator 50, thereby applying a negative pressure to the downstream suction passage 42c. The negative pressure causes evaporation of the liquid fuel within the decompression chamber 52b. Thus, in a state where the sucking operation of the aspirator 50 is stable, an increase in the vapor pressure caused by the evaporation of the liquid fuel partially offsets a decrease in the vapor pressure caused by the application of the negative pressure in the decompression chamber 52b. As a result, the internal pressure of the decompression chamber 52b enters an equilibrium state, such that the fuel vapor in the decompression chamber 52b enters a saturated state at the equilibrium pressure.

Figure 7:
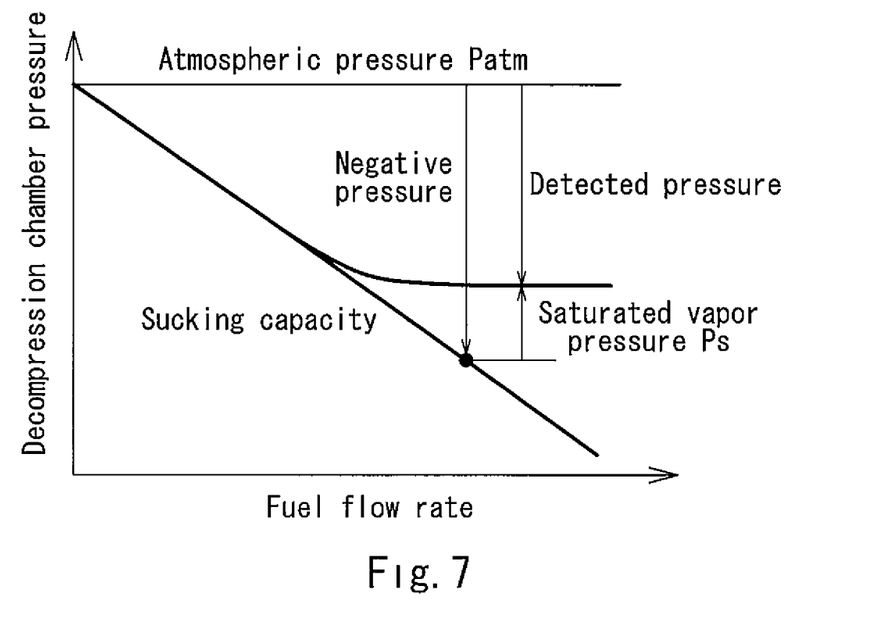
FIG. 7 is a graph showing pressure changes in a decompression chamber of an aspirator.
Figure 8:
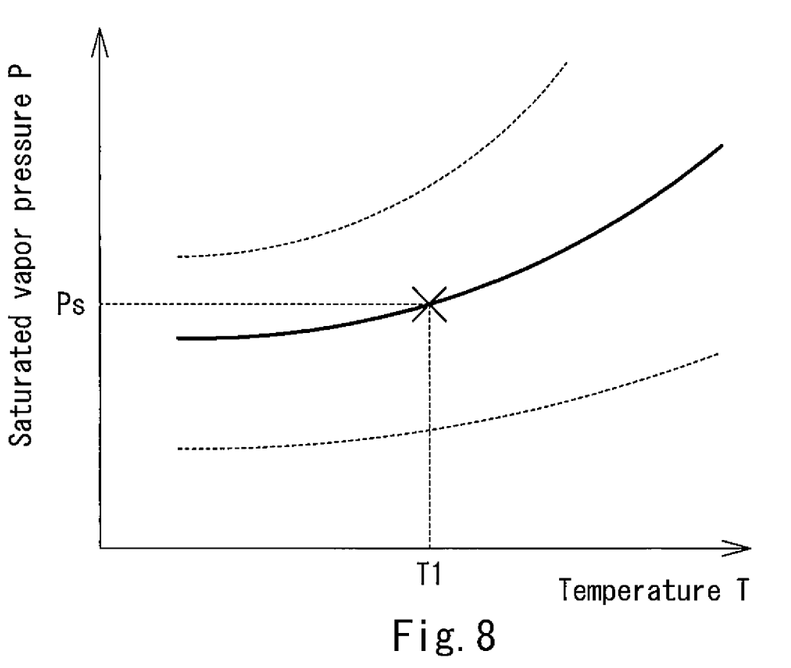
FIG. 8 is a graphs showing saturation vapor curves.

As shown in FIG. 7, the saturation vapor pressure Ps of the fuel vapor can be calculated from a difference between an expected negative pressure in the decompression chamber 52b, which is determined based on the flow rate of the liquid fuel flowing through the aspirator 50, and the actual pressure in the decompression chamber 52b, which may be measured by a differential pressure sensor 42e. The flow rate of the liquid fuel flowing through the aspirator 50 can be estimated from the rotational speed of the fuel pump 21 or the like. As shown in FIG. 8, the saturation vapor pressure curve can be specified by a specific relationship between the saturation vapor pressure Ps and the temperature T1. The temperature T1 corresponds to a temperature of the upper region of the gaseous layer in the fuel tank 20, which may be measured by the first temperature sensor 27. Once the appropriate saturation vapor pressure curve has been selected, changes in the saturation vapor pressure can be estimated from the temperature change in the gaseous layer of the fuel tank 20.

Next, fuel vapor density ρgv and air density ρatm in the gaseous mixture are estimated in order to calculate the partial pressure of the fuel vapor in the gaseous mixture within the gaseous layer of the fuel tank 20. The air density ρatm is a known fixed number. Thus, the fuel vapor density ρgv can be estimated by calculating the gaseous mixture density ρ and then subtracting the air density ρatm from the gaseous mixture density $\rho$. The gaseous mixture density $\rho$ can be calculated based on following Formula (1).

$$\Delta P = (Q/CK)^2 \rho \quad \text{Formula (1):}$$

In Formula (1), $\Delta P$ means a differential pressure between the gaseous mixture pressure before and after passing through the narrowed part 42d. The differential pressure $\Delta P$ is measured by the differential pressure sensor 42e. Q means a flow rate of the gaseous mixture. C means a flow coefficient corresponding to the flow rate Q. K means a section modulus corresponding to a radial sectional area of the narrowed part 42d.

Figure 9:
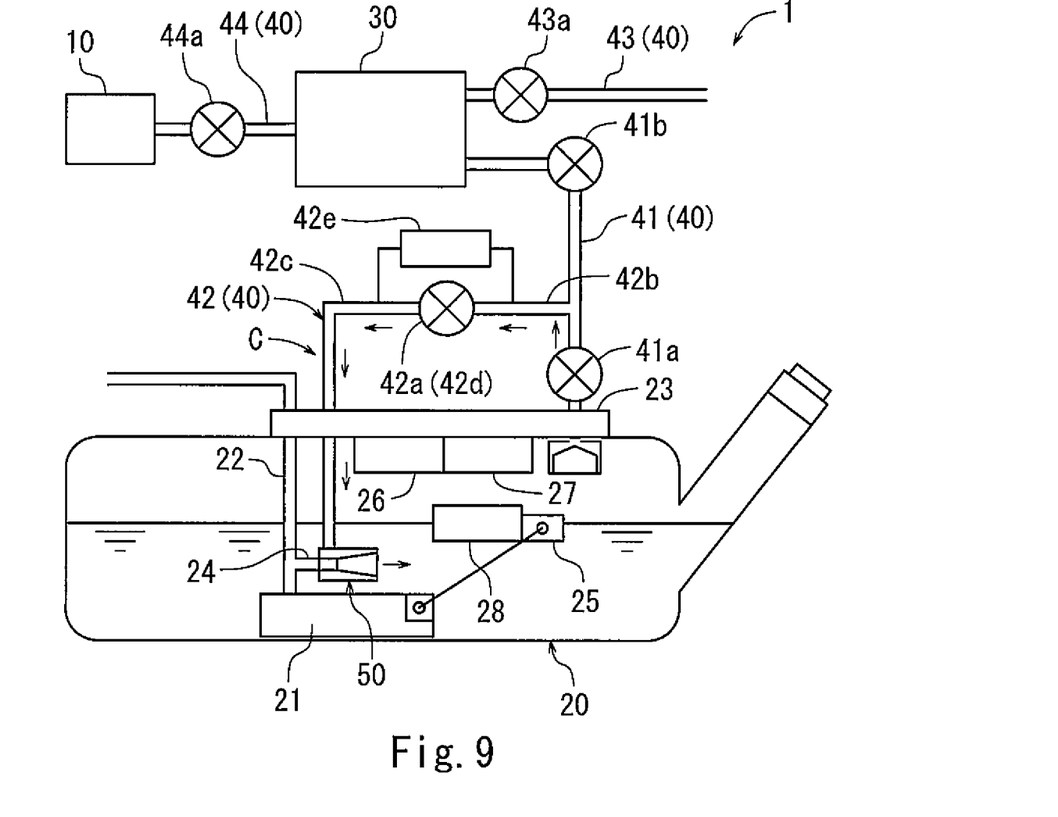
FIG. 9 is a schematic view of the fuel vapor processing system of FIG. 1 in a state where a fuel vapor concentration is estimated.

As shown in FIG. 9, in order to measure the differential pressure $\Delta P$, the shut-off valve 41a is open, the closing valve 41b is closed, and the multistage shut-off valve 42a is partially closed to form the narrowed part 42d in the suction passage 42. In such state, the fuel pump 21 is driven to operate the aspirator 50. Due to the aspiration action of the aspirator 50, the gaseous mixture flows from the gaseous layer of the fuel tank 20 through the vapor passage 41, the upstream suction passage 42b, the narrowed part 42d, the downstream suction passage 42c, and the aspirator 50, in this order. The differential pressure $\Delta P$ can be measured by the differential pressure sensor 42e as the gaseous mixture passes through the narrowed part 42d.

The ECU 60 is configured to calculate the gaseous mixture density $\rho$ based on the Formula (1). The flow rate Q of the gaseous mixture may be estimated from various parameters of the fuel pump 21, such as electric current, voltage, and/or rotational speed. Both the flow coefficient C, which corresponds to the flow rate Q, and the section modulus K, which corresponds to the radial sectional area of the narrowed part 42d, may be known values and may be stored in the memory unit 62 of the ECU 60 in advance.

The fuel vapor density $\rho gv$ can be calculated by subtracting the known air density $\rho atm$ from the calculated gaseous mixture density $\rho$. Then, the vapor partial pressure can be estimated based on a fact that the ratio of the fuel vapor density $\rho gv$ to the gaseous mixture density $\rho$ corresponds to the ratio of the fuel vapor pressure (vapor partial pressure) to the total pressure in the gaseous layer. The total pressure of the gaseous layer may be measured by the pressure sensor 26. When the estimated vapor partial pressure is less than the saturation vapor pressure corresponding to the temperature at that time, it is determined that the fuel vapor is not saturated. In this state, it is assumed that the fuel vapor pressure will increase to the saturation vapor pressure with time. On the contrary, when the estimated vapor partial pressure is greater than the saturation vapor pressure corresponding to the temperature at that time, in other words, there is a supersaturated state, it is assumed that the fuel vapor pressure will decrease to the saturation vapor pressure over time. It is thought that the rate of change of the actual vapor pressure toward the saturation vapor pressure would be proportional to the difference between the actual vapor pressure and the saturation vapor pressure. In some embodiments, the temporal changes of the fuel vapor pressure may be estimated by converting the calculated fuel vapor density $\rho gv$ to the fuel vapor concentration in the gaseous layer and then comparing this fuel vapor concentration to the saturated concentration.

When the gaseous mixture flows in the gaseous layer by convection, the rate of change of the fuel vapor pressure from the non-saturation vapor pressure to the saturation vapor pressure would be in proportion to the flow rate of the gaseous mixture in the gaseous layer, in addition to the difference between the non-saturation vapor pressure and the saturation vapor pressure. Thus, the ECU 60 is configured to estimate the convective velocity of the gaseous mixture. For estimating the convective velocity in this embodiment, the fuel pump 21 is stopped and the shut-off valve 41a and the multistage shut-off valve 42a are closed. Then, a pair of physical quantity sensors disposed in the gaseous layer measure a physical quantity in the gaseous layer. Specifically, the first temperature sensor 27 detects the temperature at the upper region of the gaseous layer, and the second temperature sensor 28 detects the temperature at the lower region of the gaseous layer. The convective velocity of the gaseous mixture corresponds to the heat flux Q generated by the thermal gradient between the upper region and the lower region of the gaseous layer. The heat flux Q can be calculated based on the following Formula (2).

$$Q = hA(T1 - T2) \quad \text{Formula (2):}$$

In the Formula (2), h means a heat transfer coefficient, A means an area of a virtual interface between the upper region and the lower region in the gaseous layer, T1 means the measured temperature of the upper region, and T2 means the measured temperature of the lower region. For this embodiment, the heat transfer coefficient h and the area A may both be considered to be fixed numbers, and thus may be stored in the ECU 60 in advance.

Figure 10:
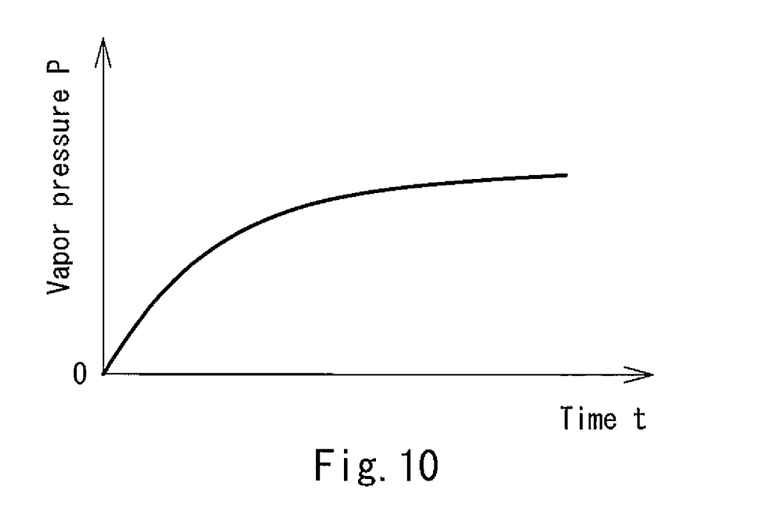
FIG. 10 is a graph showing a temporal change of the vapor pressure.
Figure 11:
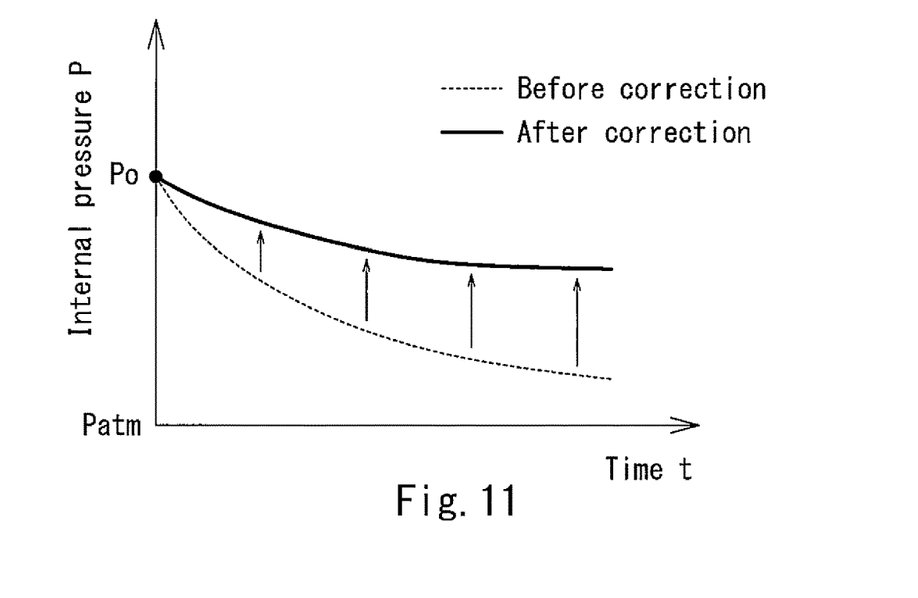
FIG. 11 is a graph showing a temporal change of an adjusted reference pressure.

After the saturated fuel vapor pressure curve, the vapor partial pressure, and the convective velocity of the gaseous mixture have been estimated, an embodiment by which was described above, the ECU 60 calculates the temporal change of the fuel vapor pressure from them. One example of the calculated temporal change of the fuel vapor pressure is shown in FIG. 10. In a case where the fuel vapor pressure increases with time, as shown in FIG. 10, the reference pressure can be corrected by adding the corresponding increment of the fuel vapor pressure to the reference pressure, as shown in FIG. 11.

Figure 12:
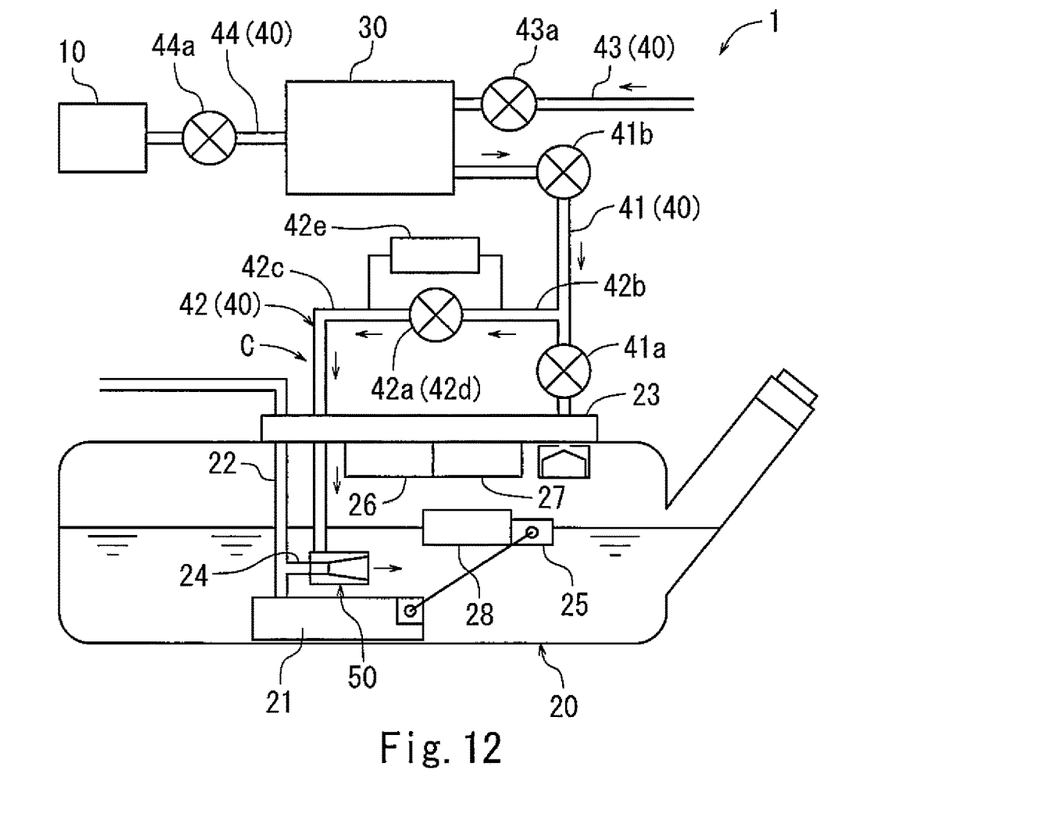
FIG. 12 is a schematic view of the fuel vapor processing system of FIG. 1 with a positive pressure introduced into the fuel tank.

After such correction of the reference pressure has been completed, a temporal change of the actual internal pressure of the fuel tank 20 is measured. As shown in FIG. 12, the closing valve 41b, the multistage shut-off valve 42a, and the atmospheric valve 43a are opened, and the shut-off valve 41a and the purge valve 44a are closed. The fuel pump 21 is driven under such state so as to forcedly feed the liquid fuel to the aspirator 50. Due to the sucking action of the aspirator 50, atmospheric air is introduced from the outside into the fuel tank 20, as shown by arrows in FIG. 12. When the internal pressure of the fuel tank 20, as detected by the pressure sensor 26, becomes the predetermined pressure P0, the fuel pump 21 is stopped, and the closing valve 41b and the multistage shut-off valve 42a are closed, such that the fluid communication between the fuel tank 20 and the outside is shut off. Then, the pressure sensor 26 detects the temporal change of the internal pressure of the fuel tank 20, after being shut off to the outside.

Figure 13:
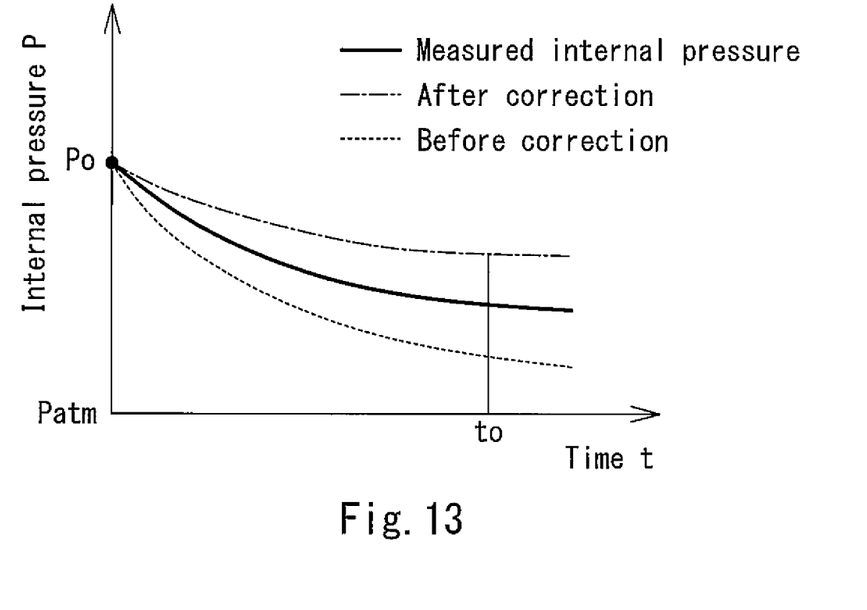
FIG. 13 is a graph showing a comparison between a detected inner pressure, the non-adjusted reference pressure, and the adjusted reference pressure.

FIG. 13 shows the measured internal pressure of the fuel tank 20, the non-corrected reference pressure, and the corrected reference pressure. In FIG. 13, the solid line is the measured internal pressure, the dotted line is the non-corrected reference pressure, and the dot-dashed line is the corrected reference pressure. At a predetermined time t0, the measured internal pressure is higher than the non-corrected reference pressure. Thus, it would erroneously be determined that the fuel tank 20 seemingly has no leakage. However, since the reference pressure has been corrected in this embodiment based on the estimated changes of the fuel vapor pressure, the measured internal pressure is determined to be lower than the corrected reference pressure. Accordingly, the ECU 60 correctly determines that fuel vapor has leaked from the fuel tank 20. Due to this configuration, vapor leakage can be detected with higher accuracy by correcting the reference pressure based on the changes in the vapor pressure.

The concentration measuring device disclosed herein is not limited to the above described embodiments, and can be variously modified without departing from the gist of the disclosure. For example, in some embodiments, a concentration measuring device includes an aspirator, a circulation passage, a fuel pump, a differential pressure sensor, and a control unit. The aspirator is disposed in a fuel tank and includes a decompression chamber. The circulation passage connects a gaseous layer in the fuel tank to the decompression chamber of the aspirator. The circulation passage includes a narrowed part having a narrower passage area than an adjacent portion of the circulation passage. The fuel pump is configured to pump a liquid fuel stored in the fuel tank to the aspirator. While the liquid fuel pumped by the fuel pump flows through an internal space of the aspirator, the aspirator generates a negative pressure in the decompression chamber so as to flow a gas containing a fuel vapor from the gaseous layer of the fuel tank through the circulation passage. The differential pressure sensor is configured to measure a pressure difference of the gas within the circulation passage between an upstream portion of the circulation passage in which the gas flows before passing through the narrowed part and a downstream portion of the circulation passage in which the gas flows after passing through the narrowed part. The control unit implemented by at least one programmed processor and is configured to calculate a density of the gas from the pressure difference of the gas, to calculate a density of the fuel vapor from the density of the gas, and to calculate a concentration of the fuel vapor from the density of the fuel vapor. In accordance with this construction, the gas flows from the gaseous layer in the fuel tank through the circulation passage and then into the fuel tank due to the negative pressure generated in the aspirator. Thus, while measuring the pressure difference of the gas, there is no heat source on the circulation passage. Accordingly, the accuracy of the concentration measurement can be improved.

In some embodiments, the concentration measuring device may further include a canister capable of adsorbing the fuel vapor evaporated in the fuel tank, and a vapor passage connecting the canister to the fuel tank. A part of the vapor passage is included in the circulation passage. In accordance with this construction, the circulation passage can be formed by using components of a fuel vapor processing system, so as to simplify the configuration of the concentration measuring device.

In some embodiments, the circulation passage may be provided with a shut-off valve capable of varying an opening amount thereof. The narrowed part is defined by the shut-off valve such that a passage area of the narrowed part varies depending on the opening amount of the shut-off valve. In accordance with this construction, the shut-off valve can open and close to control the fluid communication through the circulation passage and forms the narrowed part, thereby simplifying the configuration of the concentration measuring device.

In some embodiments, the leakage detector may be configured to detect leakage from the portions of the vapor passage that include both the fuel tank and the canister, rather than the fuel tank only. In such case, the atmospheric valve and the purge valve may be closed, and the shut-off valve and the closing valve remain open after introducing the positive pressure into the fuel tank. As such, temporal changes of the internal pressure may be measured in a state where the fuel tank and the canister are in fluid communication with each other and are shut off from the outside.

In some embodiments, the leakage may be detected by comparing temporal changes of the internal pressure to a corrected reference pressure after having introduced a negative pressure, instead of after introducing a positive pressure. In such case, the negative pressure generated by the engine may be applied to the fuel tank, so as to avoid complication of the leakage detector. In some embodiments, the saturation vapor pressure curve, the partial pressure, and the convective velocity may be estimated after introducing the positive pressure or the positive pressure may be introduced in the middle of estimation of the partial pressure or the convective velocity, so as to perform correction of the reference pressure, instead of introducing the positive pressure after correction of the reference pressure. In some embodiments, the control unit may be configured to calculate the amount of fluid discharged from the aspirator from certain parameters, such as rotational speed of the fuel pump, after estimating the partial pressure and applying the positive pressure, and to correct the partial pressure or the concentration of the fuel vapor based on the amount of fluid.

In some embodiments, the canister may be disposed in the fuel tank. In such case, the canister may be housed in a canister casing attached to and suspended from the lower surface of the set plate of the fuel tank.

In some embodiments, a pair of the temperature sensors are disposed to measure the temperature gradient in the fuel tank. For example, the pair of the temperature sensors may be spaced away from each other in the horizontal direction or both the horizontal direction and the vertical direction, instead of being spaced apart in the vertical direction only. The installation method or location of the pair of the temperature sensors is not limited. For example, the temperature sensors may be attached to an inward facing surface of the fuel tank or the canister casing. In some embodiments, at least three temperature sensor may be disposed in the fuel tank, instead of the pair of the temperature sensor, so as to increase the measurement accuracy of the temperature gradient in the gaseous layer.

In some embodiments, the circulation passage may be formed such that the fuel vapor circulates between the fuel tank and the canister. In such case, the suction passage may be positioned to extend from the canister to the aspirator, instead of branching from the vapor passage. Further, the closing valve may be disposed between the upstream suction passage and the canister.

In some embodiments, the narrowed part may have a fixed passage area defined by a venturi tube, an orifice plate, or the like, instead of the variable passage area defined by the multistage shut-off valve. In such case, an additional valve may be provided for closing the suction passage. In some embodiments, the narrowed part may be formed at the vapor passage of the circulation passage. In such case, the shut-off valve on the vapor passage may be replaced with a multistage shut-off valve.

In some embodiments, when the narrowed part has a fixed passaged area, the differential pressure sensor may be configured to measure a difference between the vapor pressure in the upstream suction passage and the vapor pressure in the narrowed part. The difference of the vapor pressure may be measured by a pair of pressure sensor, instead of the differential pressure sensor.

In some embodiments, the method for specifying the saturation vapor pressure curve may be performed by measuring pressure changes ΔP relative to temperature changes (from T1 to T2) in the gaseous layer, and looking for a saturated fuel vapor curve that corresponds to the pressure changes ΔP relative to the temperature changes (from T1 to T2) among a plurality of the saturated fuel vapor curves. In some embodiments, the temperature of the lower region of the gaseous layer, an average temperature between the temperatures of the upper region and the lower region, and/or the temperature in the decompression chamber of the aspirator may be used for specifying the saturation vapor pressure curve.

In some embodiments, an additional pump may be provided and used for feeding liquid fuel to the aspirator, instead of the fuel pump. In some embodiments, a differential pressure sensor provided at the circulation passage may be used as the second pressure sensor configured to measure the pressure in the decompression chamber of the aspirator. Alternatively, an additional pressure sensor may be provided at the downstream suction passage to function as the second pressure sensor.

In some embodiments, while the density $\rho$ of the gaseous mixture is calculated based on Formula (1), a plurality of densities $\rho$ may be calculated from a plurality of flow rates Q obtained by changing the rotational speed of the fuel pump. The influence of flow rate variations on a calculation result can thus be reduced by using an average of the calculated flow rates Q, thereby increasing the accuracy of the calculation of the density. In some embodiments, a plurality of densities $\rho$ may be measured from a plurality of the section moduli K by changing the opening degree of the multistage shut-off valve without altering the flow rate.

In some embodiments, the partial pressure of the fuel vapor may be estimated from the ratio of the fuel vapor concentration in the gaseous mixture. The fuel vapor concentration may be calculated from the density of the fuel vapor or may be measured by a concentration sensor provided at the fuel vapor processing system.

In some embodiments, the convective velocity in the gaseous layer may be interpreted to correspond to a diffusion flux J generated by the density gradient of the fuel vapor between the upper region and the lower region in the gaseous layer. The convective velocity in the gaseous layer may be calculated based on such an interpretation by using Formula (3).

$$J = -D(C1-C2) \qquad \text{Formula (3):}$$

In Formula (3), C1 means the measured density of the fuel vapor in the upper region, C2 means the measured density of the fuel vapor in the lower region, and D means a diffusion coefficient. In such case, the densities C1, C2 may be measured by a pair of concentration sensors. That is, in this embodiment, the pair of the concentration sensors are provided as the pair of the physical quantity sensors, instead of the pair of the temperature sensors. The diffusion coefficient D in Formula (3) may be considered to be a fixed number, and thus may be stored in the ECU in advance. In a case where the convective velocity is calculated from the density gradient as described above, the total number of the temperature sensors provided in the fuel tank may be one.

What is claimed is:

1. A concentration measuring device, comprising:
   an aspirator disposed in a fuel tank, the aspirator including a decompression chamber;
   a circulation passage connecting a gaseous layer in the fuel tank to the decompression chamber of the aspirator, wherein the circulation passage includes a narrowed part having a passage area narrower than an adjacent portion of the circulation passage;
   a fuel pump configured to pump a liquid fuel stored in the fuel tank to the aspirator, wherein while the liquid fuel pumped by the fuel pump flows through an internal space of the aspirator, the aspirator generates a negative pressure in the decompression chamber so as to flow a gas containing a fuel vapor from the gaseous layer of the fuel tank through the circulation passage;
   a differential pressure sensor configured to measure a pressure difference of the gas within the circulation passage between an upstream portion of the circulation passage in which the gas flows before passing through the narrowed part and a downstream portion of the circulation passage in which the gas flows after passing through the narrowed part; and
   a control unit implemented by at least one programmed processor,
   wherein the control unit is configured to calculate a density of the gas from the pressure difference of the gas, to calculate a density of the fuel vapor from the density of the gas, and to calculate a concentration of the fuel vapor from the density of the fuel vapor.

2. The concentration measuring device of claim 1, further comprising:
   a canister capable of adsorbing the fuel vapor evaporated in the fuel tank; and
   a vapor passage connecting the canister to the fuel tank, wherein a part of the vapor passage is included in the circulation passage.

3. The concentration measuring device of claim 1, wherein:
   the circulation passage is provided with a shut-off valve capable of varying an opening amount thereof, and
   the narrowed part is defined by the shut-off valve such that the passage area of the narrowed part varies depending on the opening amount of the shut-off valve.

* * * * *